(12) United States Patent
Orr (10) Patent No.: US 12,178,733 B2
(45) Date of Patent: Dec. 31, 2024

(54) ORTHOPEDIC WALKING BOOT HAVING A MECHANICALLY ADJUSTABLE RAMP INSERT

(71) Applicant: DJO, LLC, Carlsbad, CA (US)

(72) Inventor: David Orr, Vista, CA (US)

(73) Assignee: DJO, LLC, Carlsbad, CA (US)

( * ) Notice: Subject to any disclaimer, the term of this patent is extended or adjusted under 35 U.S.C. 154(b) by 0 days.

(21) Appl. No.: 18/212,965

(22) Filed: Jun. 22, 2023

(65) Prior Publication Data

US 2023/0414396 A1 Dec. 28, 2023

Related U.S. Application Data

(63) Continuation of application No. 17/465,094, filed on Sep. 2, 2021, now Pat. No. 11,690,750, which is a (Continued)

(51) Int. Cl.
*A61F 5/01* (2006.01)
*A43B 7/16* (2006.01)
(Continued)

(52) U.S. Cl.
CPC .............. *A61F 5/0195* (2013.01); *A43B 7/16* (2013.01); *A43B 7/20* (2013.01); *A43B 7/223* (2013.01);
(Continued)

(58) Field of Classification Search
CPC ...... A61F 5/012; A61F 5/0195; A61F 5/0111; A61F 5/042; A61F 5/048; A61F 5/14;
(Continued)

(56) References Cited

U.S. PATENT DOCUMENTS 4,765,070 A 8/1988 Chemello et al.
4,962,760 A 10/1990 Jones
(Continued)

FOREIGN PATENT DOCUMENTS

CN 2351003 Y 12/1999
CN 2419856 Y 2/2001
(Continued)

OTHER PUBLICATIONS

"Memory Foam Shoe Heel Cushion—Instant Comfort, Men, One Size Fits All: Health & Personal Care." Amazon.com, Amazon.com, Inc., Dec. 12, 2012. Bottom Paragraph. Www.amazon.com/Memory-Foam-Shoe-Heel-Cushion/dp/B0027IUJ7C.
(Continued)

*Primary Examiner* — Ophelia A Hawthorne
(74) *Attorney, Agent, or Firm* — Veros Legal Solutions, LLP (57) ABSTRACT

An orthopedic walking boot includes a housing configured to encompass at least a user's foot, a mechanically adjustable ramp insert including a ramp surface and disposed in the housing, an adjusting mechanism configured to adjust an elevation angle of the ramp surface, and a mechanically adjustable lift configured to cause the mechanically adjustable ramp insert to descend within the housing as the ramp surface is elevated such that vertical displacement of the user's foot caused by elevation of the ramp surface is substantially attenuated. Related methods are also provided.

19 Claims, 6 Drawing Sheets

Related U.S. Application Data continuation of application No. 16/393,683, filed on Apr. 24, 2019, now Pat. No. 11,109,993, which is a continuation of application No. PCT/US2017/060663, filed on Nov. 8, 2017.

(60) Provisional application No. 62/419,825, filed on Nov. 9, 2016.

(51) Int. Cl.
*A43B 7/20* (2006.01)
*A43B 7/22* (2006.01)
*A61F 5/042* (2006.01)
*A61F 5/048* (2006.01)
*A61F 5/14* (2022.01)

(52) U.S. Cl.
CPC ............ *A61F 5/0111* (2013.01); *A61F 5/042* (2013.01); *A61F 5/048* (2013.01); *A61F 5/14* (2013.01)

(58) Field of Classification Search
CPC .... A61F 5/32; A43B 7/16; A43B 7/20; A43B 5/0437; A43B 7/143; A43B 7/142; A43B 7/223
USPC ............................................................ 36/88
See application file for complete search history.

(56) References Cited

U.S. PATENT DOCUMENTS

| | | | |
|---|---|---|---|
| 7,563,238 B1 | 7/2009 | Breashears | |
| 2004/0064195 A1 | 4/2004 | Herr | |
| 2005/0108900 A1 | 5/2005 | Knowles | |
| 2010/0065795 A1 | 3/2010 | Christie | |
| 2010/0069807 A1 | 3/2010 | Cox | |
| 2011/0313336 A1 | 12/2011 | Chan | |
| 2012/0000092 A1 | 1/2012 | Ingvarsson et al. | |
| 2014/0350446 A1* | 11/2014 | Gunnsteinsson | ........ A43B 7/16 602/27 |
| 2021/0393431 A1 | 12/2021 | Orr | |

FOREIGN PATENT DOCUMENTS

| | | |
|---|---|---|
| CN | 1358465 A | 7/2002 |
| CN | 201379121 Y | 1/2010 |
| CN | 104225903 A | 12/2014 |
| CN | 105615138 A | 6/2016 |
| EP | 2588043 A1 | 5/2013 |
| JP | 853062516 | 8/2021 |
| KR | 20040105673 A | 12/2004 |
| KR | 20130103862 A | 9/2013 |
| WO | 2006094383 A2 | 9/2006 |
| WO | 2016067229 A1 | 5/2016 |

OTHER PUBLICATIONS

European Patent Office, Extended European Search Report and Opinion, May 29, 2020, Munich, Germany.
International Search Report and Written Opinion mailed Feb. 1, 2018 in PCT/US2017/060663.

* cited by examiner

ORTHOPEDIC WALKING BOOT HAVING A MECHANICALLY ADJUSTABLE RAMP INSERT

CROSS REFERENCE TO RELATED APPLICATIONS

This application is a continuation of U.S. patent application Ser. No. 17/465,094, filed on Sep. 2, 2021, which is a continuation of U.S. patent application Ser. No. 16/393,683, filed on Apr. 24, 2019, which is a continuation of International Patent Application No. PCT/US2017/060663, filed on Nov. 8, 2017, which claims the benefit of U.S. Provisional Application No. 62/419,825, which was filed on Nov. 9, 2016. Applicant hereby incorporates the contents of these applications in their entirety.

BACKGROUND

Field of the Disclosure

The present application is directed to orthopedic walking boots for treating lower leg injuries. More specifically, the present application is directed to orthopedic walking boots having a mechanically adjustable ramp insert.

Description of Related Technology

Orthopedic braces are often used to provide support to injured limbs. For example, ankle braces, knee braces and wrist braces are used when a bone is fractured or a ligament or tendon is sprained, or under conditions of arthritis or other injuries to aid a patient's recovery by supporting the injured area until it heals and regains strength. Some braces provide support that allows a user to position the foot of the injured limb in discrete angles of plantarflexion utilizing multiple insertable heel wedges. Some other braces provide plantarflexion or dorsiflexion at discrete angles (i.e., in multiples of 7.5 degrees) by allowing adjustment of the elevation angle of the entire foot portion of the brace with respect to the upper, leg portion of the brace. However, the use of such heel wedges and/or discrete-angle brace designs do not allow for continuous adjustment of the elevation angle of plantarflexion. Accordingly, walking braces providing customizable continuous adjustment of an angle of plantarflexion are desirable.

SUMMARY

An orthopedic walking boot is provided. The orthopedic walking boot includes a housing configured to encompass at least a user's foot. The orthopedic walking boot includes a mechanically adjustable ramp insert comprising a ramp surface and disposed in the housing. The orthopedic walking boot includes an adjusting mechanism configured to adjust an elevation angle of the ramp surface.

A method for adjusting an orthopedic walking boot is provided. The method includes adjusting an adjusting mechanism disposed on a housing of the orthopedic walking boot thereby achieving a desired elevation angle of a ramp surface of a mechanically adjustable ramp insert of the orthopedic walking boot. The method includes inserting a user's foot into the housing and disposing the user's foot on the ramp surface such that the user's foot is supported in a position of plantarflexion determined at least in part by the desired elevation angle of the ramp surface.

BRIEF DESCRIPTION OF THE DRAWINGS

The foregoing and other objects and advantages will be appreciated more fully from the following description, with reference to the accompanying drawings. These depicted embodiments are to be understood as illustrative and not as limiting in any way.

DETAILED DESCRIPTION

To provide an overall understanding of the devices and methods described herein, certain illustrative embodiments will now be described. For the purpose of clarity and illustration, these devices and methods will be described with respect to an orthopedic walking boot applied to a user's lower leg and ankle. It will be understood by one of ordinary skill in the art that the devices and methods described herein may be adapted and modified as appropriate. These devices and methods may be employed in other suitable applications, such as for other types of braces that include other such additions and modifications that will not depart from the scope hereof.

Figure 1:
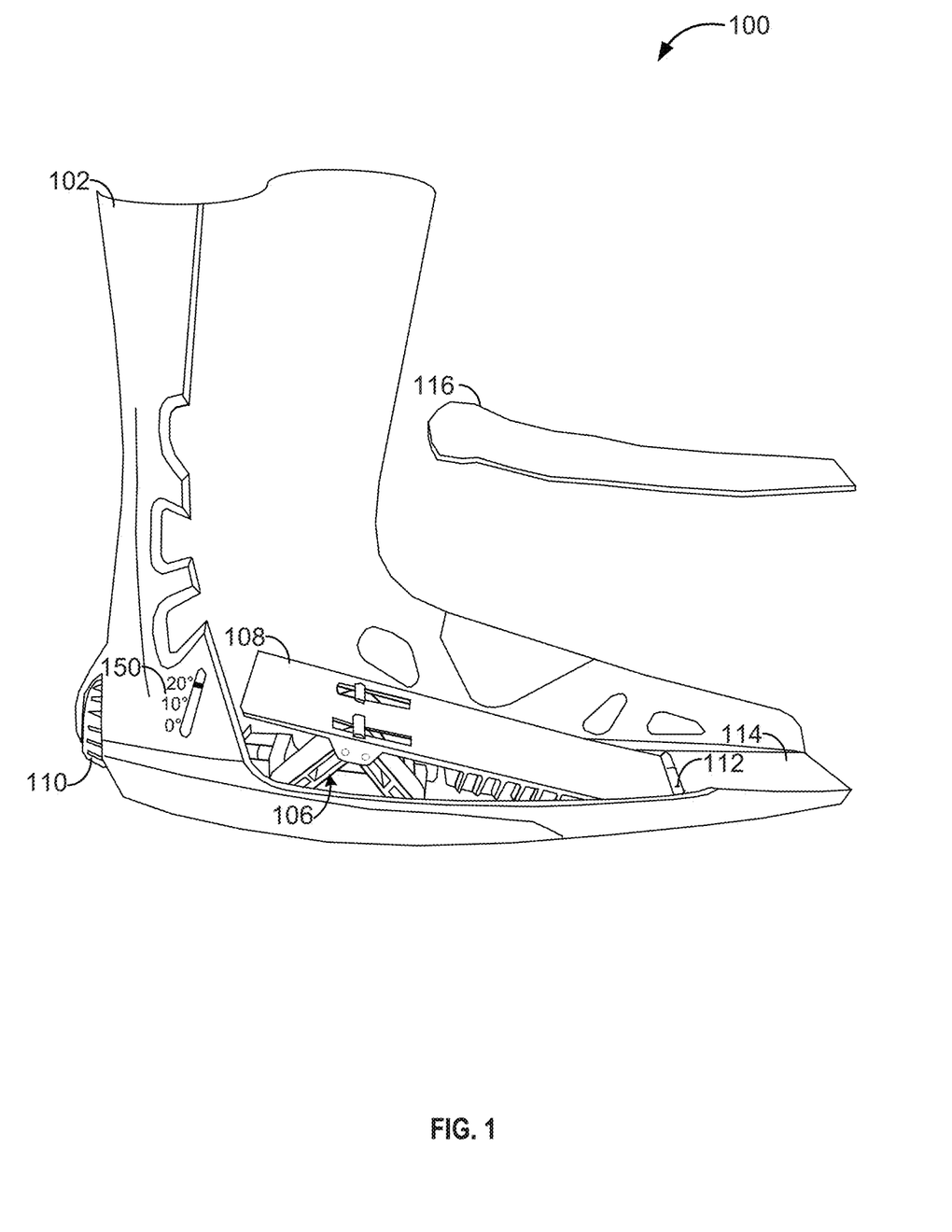
FIG. 1 illustrates a simplified cutaway diagram of an orthopedic walking boot having a mechanically adjustable ramp insert allowing continuously variable angles of plantarflexion, in accordance with some embodiments.

FIG. 1 illustrates a simplified cutaway diagram of an orthopedic walking boot 100 having a mechanically adjustable ramp insert 106 allowing continuously variable angles of plantarflexion, in accordance with some embodiments. Walking brace 100 includes a housing 102 configured to encompass at least a user's foot (foot not shown in FIG. 1). In some embodiments, housing 102 may comprise a lightweight material providing sufficient strength to support the user's foot, such as plastic, metal, or any other sufficiently strong and light-weight material. Walking brace 100 further includes a mechanically adjustable ramp insert 106 comprising a ramp surface 108 and disposed in housing 102. In some implementations, a user's entire foot may be disposed on the ramp surface 108. In some embodiments, mechanically adjustable ramp insert 106 further comprises an anterior portion 114 and a hinge 112 that physically couples anterior portion 114 to ramp surface 108. Where mechanically adjustable ramp insert 106 comprises both ramp surface 108 and anterior portion 114, a user's toes and potentially the ball of the user's foot may be disposed on anterior portion 114, while the arch and heel of the user's foot may be disposed on ramp surface 108. Walking brace 100 further includes an adjusting mechanism 110 disposed on housing 102 and configured to rotate. In some implementations, adjusting mechanism 110 comprises a dial. Rotation of adjusting mechanism 110 in one of a clockwise direction or a counter-clockwise direction causes mechanically adjustable ramp insert 106 to elevate ramp surface 108 at an angle θ. Due to the continuously adjustable (e.g., rotatable) configuration of adjusting mechanism 110, the elevation angle θ is continuously variable within a range of angles, e.g., between approximately 0 degrees to approximately 30 degrees, although the present application is not so limited and any angle of plantarflexion is contemplated. In some embodiments, walking brace 100 further includes an indicator 150 disposed on housing 102 and configured to indicate the elevation angle θ of ramp surface 108. Indicator 150 may be mechanically or electrically coupled to ramp surface 108 or mechanically adjustable ramp insert 106 in a way that allows proper display of the indication of the elevation angle θ. Continuously elevating ramp surface 108 to a desired angle θ results in a proportional degree of plantarflexion of the user's foot when the user's foot is disposed on ramp surface 108, thereby relieving tension and/or stress on the user's Achilles tendon.

In some embodiments, walking brace 100 may further include an insole 116 configured to be removably attached to and/or disposed on mechanically adjustable ramp insert 106 within housing 102. For example, insole 116 may be disposed on mechanically adjustable ramp insert 106 by friction, by a fastener such as Velcro, buttons, snaps, or the like, or by any other removable attachment method currently known or unknown. In some embodiments, insole 116 is constructed from a memory foam material. In some other embodiments, insole 116 may be constructed from another cushioning material, such as Styrofoam balls, bean bag materials, a solid or viscous gel, rubber, foam, etc.

Figure 2:
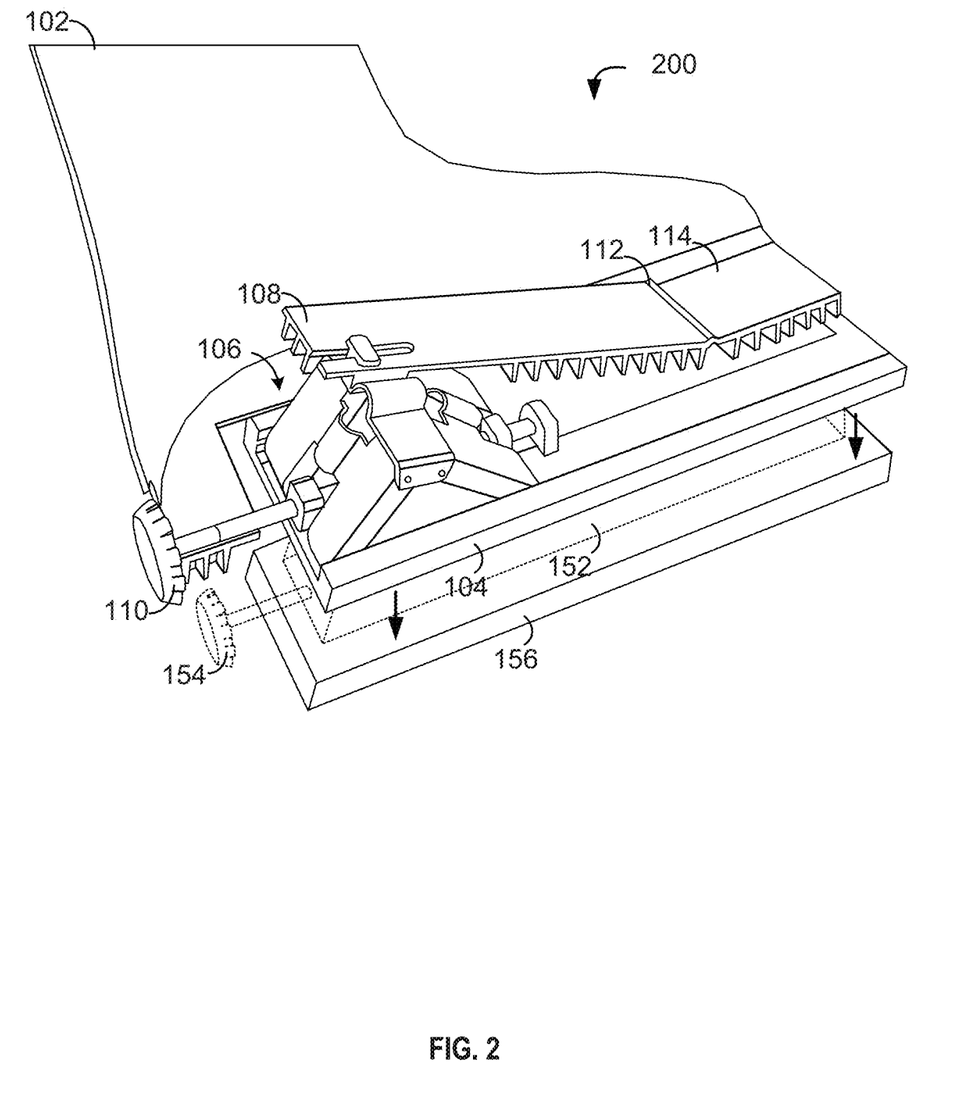
FIG. 2 illustrates another simplified cutaway diagram of the orthopedic walking boot of FIG. 1, in accordance with some embodiments.

FIG. 2 illustrates another simplified cutaway diagram 200 of orthopedic walking boot 100 of FIG. 1, in accordance with some embodiments. Diagram 200 shows housing 102, and mechanically adjustable ramp insert 106 comprising ramp surface 108, anterior portion 114, and hinge 112. Diagram 300 shows only a portion of ramp surface 108, anterior portion 114, and hinge 112 so as to provide an unobstructed visualization of adjusting mechanism 110 coupled to mechanically adjustable ramp insert 106, and of a base 104 of mechanically adjustable ramp insert 106. In some embodiments, base 104 may be an integral part of housing 102 and/or of walking brace 100. For example, housing 102 may be molded or formed so as to include the features of base 104 in a monolithic form. In some other embodiments, base 104 is a separate component apart from housing 102 within walking brace 100.

In some embodiments, walking brace 100 further comprises a foundation 156 and a mechanically adjustable lift 152 disposed on foundation 156. As shown by the double arrows pointing downward, mechanically adjustable lift 152 may be configured to adjust an elevation of base 104, and so of mechanically adjustable ramp insert 106 as a whole, within housing 102 as ramp surface 108 is elevated such that vertical displacement of the user's foot (for example the displacement of the user's heel with respect to a non-elevated position) caused by elevation of ramp surface 108 by mechanically adjustable ramp insert 106 is substantially attenuated or eliminated. Mechanically adjustable lift 152 may be configured to cause mechanically adjustable ramp insert 106 to uniformly descend within housing 102 in proportion to the degree of elevation of a point on ramp surface 108. Mechanically adjustable lift 152, shown as a dotted line box, may comprise any lifting mechanism, for example, a hydraulic, pneumatic, mechanical or electrical lift, configurable to provide the operation as described above. In some implementations, mechanically adjustable lift 152 may comprise a mechanism similar or substantially the same as that described for mechanically adjustable ramp insert 106. In some embodiments, mechanically adjustable lift 152 may be controlled based on the degree of elevation of ramp surface 108 (e.g., based on a position of adjusting mechanism 110). In some other embodiments, mechanically adjustable lift 152 may be controlled utilizing a separate adjusting mechanism 154. Such a configuration may allow for ergonomic positioning of the user's foot regardless of the elevation angle of elevation.

Figure 3:
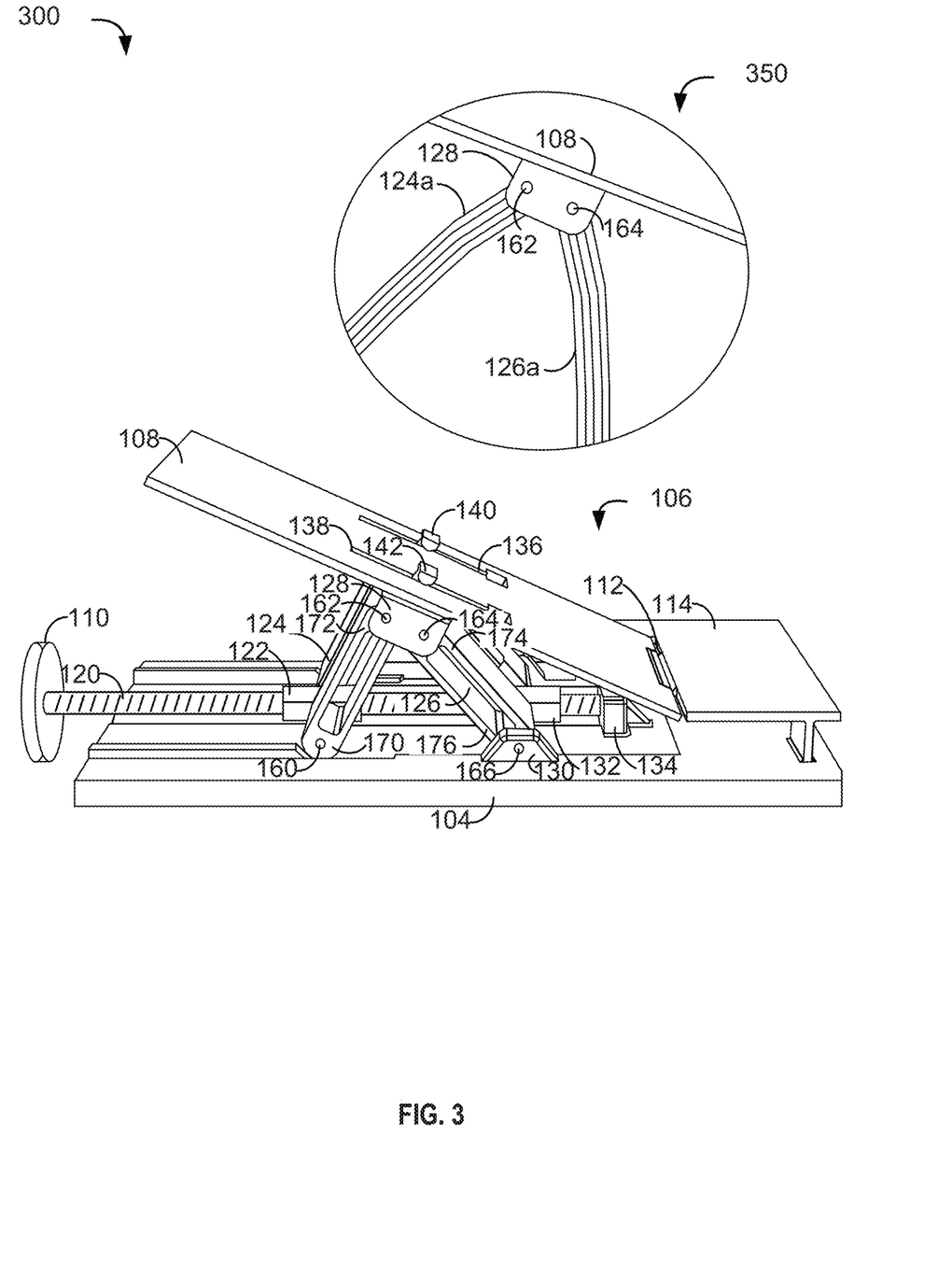
FIG. 3 illustrates a diagram of a mechanically adjustable ramp insert of the orthopedic walking boot of FIG. 1 and a callout illustrating a multi-ply leaf spring integrated into the mechanically adjustable ramp insert, in accordance with some embodiments.

FIG. 3 illustrates a diagram 300 of a mechanically adjustable ramp insert 106 of orthopedic walking boot 100 of FIG. 1 and a callout 350 illustrating a multi-ply leaf spring integrated into the mechanically adjustable ramp insert 106, in accordance with some embodiments. Mechanically adjustable ramp insert 106 may include a threaded shaft 120 secured to adjusting mechanism 110 at a first end and configured to rotate with adjusting mechanism 110. Threaded shaft 120 may comprise a hard plastic, metal, or any other material with sufficient strength to ensure the threads do not deform under mechanical stresses expected to occur during use of mechanically adjustable ramp insert 106. Mechanically adjustable ramp insert 106 further includes a first slider nut 122 comprising internal threads (not shown in FIG. 3) which mesh with the threads of threaded shaft 120. First slider nut 122 is configured to move along threaded shaft 120 as threaded shaft 120 is rotated. In some embodiments, mechanically adjustable ramp insert 106 further comprises a stationary nut 132 in physical contact with threaded shaft 120. In such embodiments, stationary nut 132 is configured to not move along threaded shaft 120 as the threaded shaft is rotated.

In some alternative embodiments, stationary nut 132 is replaced by a second slider nut (not shown, but would replace stationary nut 132) comprising internal threads (not shown in FIG. 3). In such embodiments, the second slider nut may be configured to move along threaded shaft 120 in a direction opposite of the motion of first slider nut 122 such that first slider nut 122 and the second slider nut move toward each other as threaded shaft 120 rotates. In such alternative embodiments, a first portion of threaded shaft 120 on which first slider nut 122 moves may comprise threads that curl around threaded shaft 120 in a direction opposite of threads of a second portion of threaded shaft 120 on which the second slider nut moves. Likewise, the internal threads of the second slider nut may be in physical contact with and configured to mesh with the threads of the second portion of threaded shaft 120. Such a configuration enables the second slider nut to move along threaded shaft 120 in a direction opposite of the motion of first slider nut 122.

Mechanically adjustable ramp insert 106 further comprises a bracket 128 in physical contact with ramp surface 108. Mechanically adjustable ramp insert 106 further comprises a first support 124 coupled to first slider nut 122 at a first end and to bracket 128 at a second end. First end 170 of first support 124 may be coupled to first slider nut 122 by a first movable joint 160 and second end 172 of first support 124 may be coupled to bracket 128 by a second movable joint 162.

Mechanically adjustable ramp insert 106 further comprises a second support 126 coupled to base 104 (e.g., via a bracket 130) at a first end and to bracket 128 at a second end. First end 176 of second support 126 may be coupled to base 104 (e.g., at bracket 130) by a third movable joint 166 and second end 174 of second support 126 may be coupled to bracket 128 by a fourth movable joint 164. Such a configuration may result in first end 170 of first support 124 being configured to move toward first end 176 of second support 126, thereby causing mechanically adjustable ramp insert 106 to elevate ramp surface 108.

Mechanically adjustable ramp insert 106 further comprises a stopper 134 in physical contact with a second end of threaded shaft 120 and configured to restrict movement of threaded shaft 120 in any direction normal to a plane of rotation of threaded shaft 120. Ramp surface 108 comprises at least one guide 136, 138 and bracket 128 comprises at least one peg 140, 142. The at least one peg 140, 142 of bracket 128 is configured to slide along the at least one guide 136, 138 as ramp surface 108 is elevated. In some embodiments, the at least one guide 136, 138 comprises a slot disposed in ramp surface 108. Although illustrated as rising above the plane of ramp surface 108, in some embodiments, the at least one peg 140, 142 of bracket 128 and/or the at least one guide 136, 138 may be shaped such that the at least one peg 140, 142 is countersunk in and/or does not rise about a top surface of ramp surface 108.

In some embodiments, as shown in callout 350, one or both of first support 124 and second support 126 may comprise a multi-ply leaf spring 124a and 126a, respectively, configured to attenuate a portion of physical loads that are transmitted to the user's foot when the user is walking. As shown in callout 350, first support as a multi-ply leaf spring 124a may be fixed to bracket 128 by second moveable joint 160 and second support as a multi-ply leaf spring 126a may be fixed to bracket 128 by fourth moveable joint 164. As previously described, bracket 128 may be in physical contact with ramp surface 108. Each component of mechanically adjustable ramp insert 106 described in connection with FIG. 3 may comprise hard plastic, metal, or any other material with sufficient strength to ensure the components do not deform or break under mechanical stresses expected to occur during use of mechanically adjustable ramp insert 106.

Figure 4:
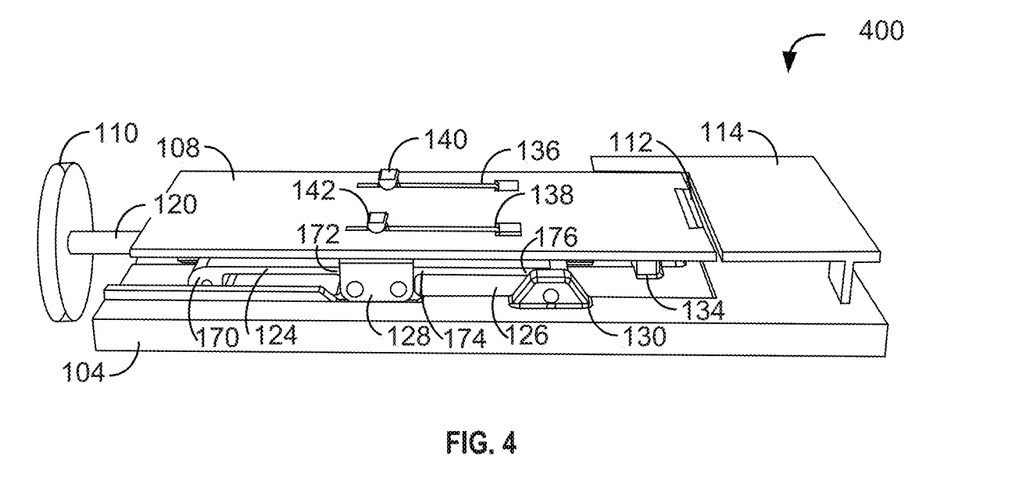
FIG. 4 illustrates another diagram of the mechanically adjustable ramp insert of FIG. 3 in a non-elevated position, in accordance with some embodiments.

FIG. 4 illustrates another diagram 400 of the mechanically adjustable ramp insert 106 of FIG. 3 in a non-elevated position, in accordance with some embodiments. Diagram 400 illustrates components of mechanically adjustable ramp insert 106 as previously described in connection with FIG. 3, however, with ramp surface 108 disposed in a fully non-elevated position (e.g., ramp surface 108 is substantially flat). As shown, first support 124 and second support 126 are in a substantially horizontal disposition. As illustrated in FIG. 4, a user's foot would be in a position of substantially no plantarflexion when disposed on ramp surface 108.

Figure 5:
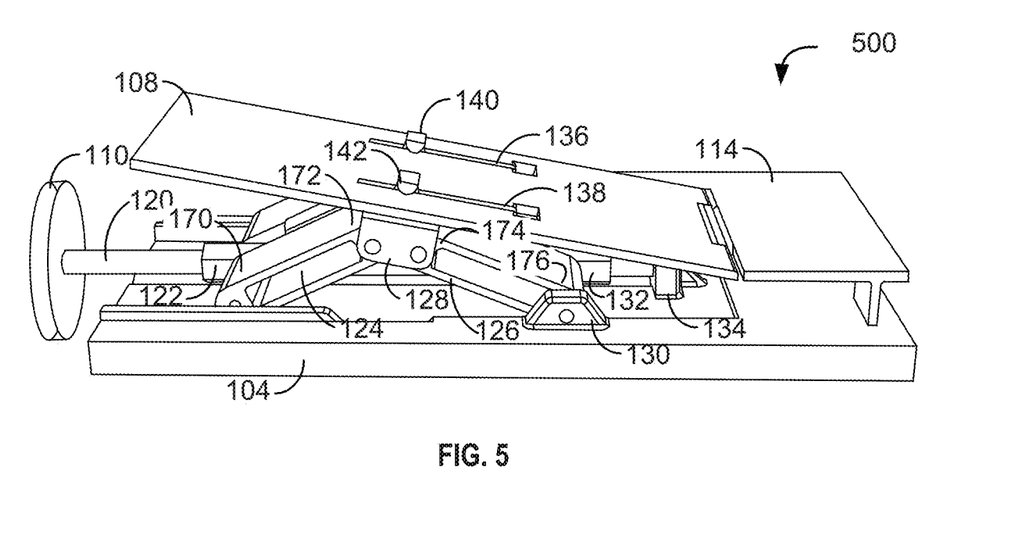
FIG. 5 illustrates another diagram of the mechanically adjustable ramp insert of FIG. 3 in an elevated position, in accordance with some embodiments.

FIG. 5 illustrates another diagram 500 of the mechanically adjustable ramp insert 106 of FIG. 3 in an elevated position having an angle of elevation greater than substantially 0 degrees, as illustrated in FIG. 4, but less than the angle of elevation illustrated in FIG. 3, in accordance with some embodiments. Diagram 400 illustrates components of mechanically adjustable ramp insert 106 as previously described in connection with FIGS. 3 and 4, however, with ramp surface 108 disposed in an intermediately elevated position (e.g., ramp surface 108 is elevated at an angle greater than 0 degrees, as shown in FIG. 4, and less than the angle of elevation shown in FIG. 3). As shown, first end 170 of first support 124 and first end 176 of second support 126 are disposed closer to each other than in FIG. 4 and ramp surface 108 is thereby elevated. As illustrated in FIG. 5, a user's foot would be in a position of intermediate plantarflexion when disposed on ramp surface 108.

Figure 6:
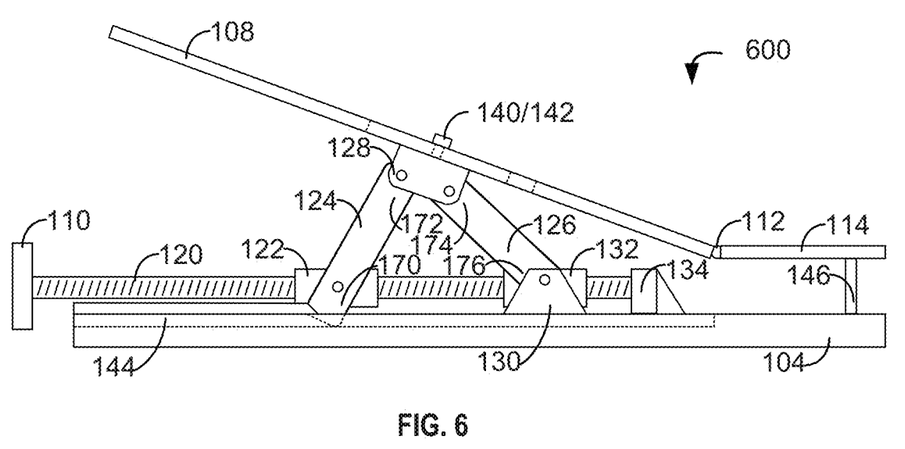
FIG. 6 illustrates a profile view diagram of mechanically adjustable ramp insert of FIG. 3, in accordance with some embodiments.

FIG. 6 illustrates a profile view diagram 600 of mechanically adjustable ramp insert 106 of FIG. 3, in accordance with some embodiments. Diagram 600 illustrates all components of mechanically adjustable ramp insert 106 previously described in connection with FIGS. 3-5, however, more clearly illustrating a third support 146 configured to fix anterior portion 114 to base 104. Diagram 600 further clearly illustrates how base 104 comprises at least one guide 144 within which at least first end 170 of first support 124 is configured to travel as ramp surface 108 is elevated. In some embodiments, guide 144 may extend at least to all portions of base 104 along which first end 170 of first support 124 is configured to travel. In some other embodiments, guide 144 may extend from an edge of base 104 closest to adjusting mechanism 110 to stopper 134. In some other embodiments, where stationary nut 132 is replaced with the second sliding nut, guide 144 may extend to all portions of base 104 along which first end 170 of first support 124 is configured to travel and to all portions of base 104 along which first end 176 of second support 126 is configured to travel. In embodiments where first end 176 of second support 126 is configured to travel, first end 176 of second support 126 would not necessarily be coupled to base 104 (e.g., via bracket 130).

Figure 7:
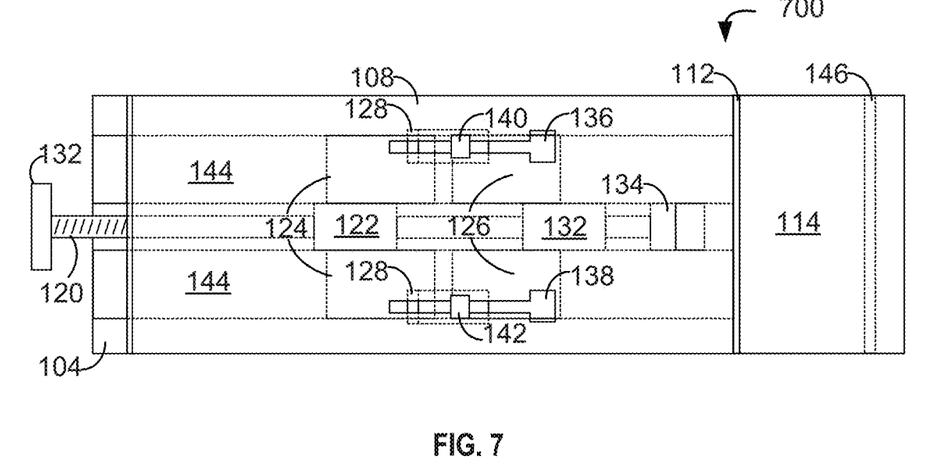
FIG. 7 illustrates a plan view diagram of mechanically adjustable ramp insert of FIG. 3, in accordance with some embodiments.

FIG. 7 illustrates a plan view diagram 700 of mechanically adjustable ramp insert of FIG. 3, in accordance with some embodiments. Diagram 700 illustrates all components of mechanically adjustable ramp insert 106 as previously described in connection with FIGS. 3-6. Dotted lines indicate outlines of variously numerated structures that would be hidden in such a real view by ramp surface 108 or anterior portion 114 of mechanically adjustable ramp insert. Moreover, diagram 700 more clearly illustrates that first support 124 and second support 126 may each comprise portions on either side of first sliding nut 122 and stationary nut 132 (or second sliding nut), respectively.

Figure 8:
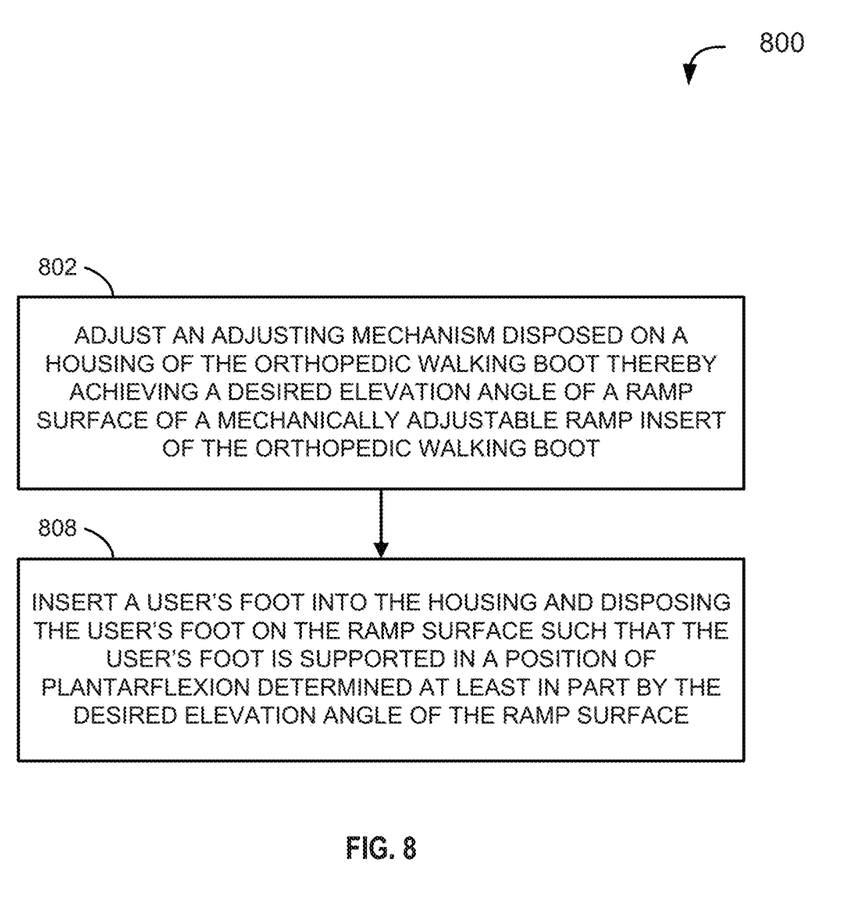
FIG. 8 illustrates a flowchart for adjusting an orthopedic walking boot, in accordance with some embodiments.

FIG. 8 illustrates a flowchart 800 for adjusting an orthopedic walking boot, in accordance with some embodiments. For example, steps in flowchart 800 may be performed utilizing walking brace 100 as previously described in connection with any of FIGS. 1-7. In some embodiments, a user of walking brace 100 is being treated for an injury to his or her Achilles tendon.

Flowchart 800 comprises step 802, which includes adjusting an adjusting mechanism 110 disposed on a housing 102 of the orthopedic walking boot 100 thereby achieving a desired elevation angle θ of a ramp surface 108 of a mechanically adjustable ramp insert 106 of the orthopedic walking boot 100. Rotating adjusting mechanism 110 causes the mechanically adjustable ramp insert 106 to elevate ramp surface 108 to the desired elevation angle θ. The desired elevation angle θ is continuously variable within a range of angles, for example, approximately 0 degrees to approximately 30 degrees.

Within mechanically adjustable ramp insert 106, rotating adjusting mechanism 100 causes threaded shaft 120 secured to adjusting mechanism 110 at a first end to rotate with adjusting mechanism 110, first slider nut 122 comprising internal threads in physical contact with threaded shaft 120 to move along threaded shaft 120 as threaded shaft 120 is rotated, and a first end 170 of first support 124 coupled to first slider nut 122 to move toward a first end 176 of second support 126 coupled to base 104. A second end 172 of first support 124 and a second end 174 of second support 126 are both coupled to bracket 128, wherein bracket 128 is in physical contact with ramp surface 108 thereby causing mechanically adjustable ramp insert 106 to elevate ramp surface 108.

In some embodiments, continuously rotating adjusting mechanism 110 causes at least first end 170 of first support 124 to travel along guide 144 of base 104 as ramp surface 108 is elevated. In some embodiments, continuously rotating adjusting mechanism 110 does not result in movement of threaded shaft 120 in any direction normal to a plane of rotation of threaded shaft 120 based on physical restriction provided by stopper 134 in physical contact with a second end of threaded shaft 120. In some embodiments, continuously rotating adjusting mechanism 110 causes at least one peg 140, 142 of bracket 128 to slide along at least one guide 136, 138 of ramp surface 108 as ramp surface 108 is elevated. In some embodiments, continuously rotating adjusting mechanism 110 causes indicator 150 disposed on housing 102 to indicate the actual angle θ of elevation of ramp surface 108 with respect to base 104 of orthopedic walking boot 100. In some embodiments, continuously rotating adjusting mechanism 110 further causes base 104 to descend within housing 102 as ramp surface 104 is elevated such that vertical displacement of the user's foot caused by elevation of ramp surface 108 is substantially attenuated or eliminated.

Flowchart 800 further comprises step 804, which includes inserting a user's foot into the housing 102 and disposing the user's foot on the ramp surface 108 such that the user's foot is supported in a position of plantarflexion determined at least in part by the desired elevation angle θ of the ramp surface 108. Step 804 may be performed before or after step 802. For example, the user's foot may first be inserted into housing 102 and then the elevation angle adjusted. Contrariwise, the elevation angle θ may be adjusted first, and the user's foot may be inserted into housing 102 after the desired angle of elevation has been achieved. Alternatively, adjustment of the elevation angle θ may also occur both before and after insertion of the user's foot into housing 102.

The methods disclosed herein include one or more actions for achieving the described method. The method and/or actions can be interchanged with one another without departing from scope of claims. In other words, unless a specific order of actions is specified, order and/or use of specific actions can be modified without departing from the scope of claims.

It is to be understood that the foregoing description is merely illustrative and is not to be limited to details given herein. While several embodiments have been provided in present disclosure, it should be understood that the disclosed devices and methods and their components may be embodied in many other specific forms without departing from the scope of disclosure.

Various modifications will occur to those of skill in art after reviewing this disclosure. The disclosed features may be implemented in any combination and subcombinations (including multiple dependent combinations and subcombinations) with one or more features described herein. The various features described or illustrated above including any components thereof may be combined or integrated into other systems. Moreover, certain features may be omitted or not implemented. Examples of changes, substitutions and alterations are ascertainable by one skilled in art and could be made without departing from the scope of information disclosed herein. All references cited herein are incorporated by reference in their entirety and made part of this application.

In the present disclosure, certain terminology is used in following ways. The singular forms "a," "an," and "the" include plural referents unless context clearly dictates otherwise. Thus, for example, reference to an item includes reference to one or more items. The term "ones" refers to one, two, or more, and generally applies to selection of some or all of a quantity. The term "plurality" refers to two or more of an item. The term "about" means quantities, dimensions, sizes, formulations, parameters, shapes and other characteristics need not be exact, but can be approximated and/or larger or smaller, as desired, reflecting acceptable tolerances, conversion factors, rounding off, measurement error and the like and other factors known to those of skill in the art. The term "substantially" means that recited characteristic, parameter, or value need not be achieved exactly, but that deviations or variations including, for example, tolerances, measurement error, measurement accuracy limitations and other factors known to those of skill in the art, can occur in amounts that do not preclude the effect the characteristic was intended to provide.

Numerical data can be expressed or presented herein in a range format. It is to be understood that such a range format is used merely for convenience and brevity and thus should be interpreted flexibly to include not only numerical values explicitly recited as limits of the range, but also interpreted to include all of the individual numerical values or sub-ranges encompassed within that range as if each numerical value and sub-range is explicitly recited. As an illustration, a numerical range of "approximately 0 degrees to approximately 30 degrees" should be interpreted to include not only the explicitly recited values of approximately 0 degrees to approximately 30 degrees, but also include the individual values and sub-ranges within the indicated range. Thus, included in this numerical range are individual values such as 10, 20 and 25 and sub-ranges such as 0-10, 10-20 and 20-30, etc. This same principle applies to ranges reciting only one numerical value (e.g., "greater than about 1") and should apply regardless of breadth of range or characteristics being described. A plurality of items can be presented in a common list for convenience. However, these lists should be construed as though each member of the list is individually identified as a separate and unique member. Thus, no individual member of such a list should be construed as a de facto equivalent of any other member of the same list solely based on their presentation in a common group without indications to the contrary. Furthermore, where terms "and" and "or" are used in conjunction with a list of items, they are to be interpreted broadly, in that any one or more of listed items can be used alone or in combination with other listed items. The term "alternatively" refers to the selection of one of two or more alternatives, and is not intended to limit selection to only those listed alternatives or to only one of the listed alternatives at a time, unless context clearly indicates otherwise. The term "coupled" as used herein does not require that components be directly connected to each other. Instead, the term is intended to also include configurations with indirect connections where one or more other components can be included between coupled components. Also, as used herein, including in the claims, "or" as used in a list of items prefaced by "at least one of" indicates a disjunctive list such that, for example, a list of "at least one of A, B, or C" means A or B or C or AB or AC or BC or ABC (i.e., A and B and C). Further, the term "exemplary" does not mean that the described example is preferred or better than other examples. As used herein, a "set" of elements is intended to mean "one or more" of those elements, except where the set is explicitly required to have more than one or explicitly permitted to be a null set.

Various changes, substitutions, and alterations to techniques described herein can be made without departing from the technology of the teachings as defined by the appended claims. Moreover, the scope of the disclosure and the claims is not limited to particular aspects of any process, machine, manufacture, composition of matter, means, methods, and actions described above. Processes, machines, manufacture, compositions of matter, means, methods, or actions, presently existing or later to be developed, that perform substantially the same function or achieve substantially the same result as corresponding aspects described herein can be utilized. Accordingly, the appended claims include within their scope such processes, machines, manufacture, compositions of matter, means, methods, or actions.

What is claimed is:

1. An orthopedic walking boot, comprising:
    a housing configured to encompass at least a user's foot;
    a mechanically adjustable ramp insert disposed in the housing and comprising:
        a base,
        a ramp surface comprising at least one guide,
        a bracket configured to slide along the at least one guide as the ramp surface is elevated,
        a first support rotatably coupled to the bracket and disposed between the base and the ramp surface; and
        a second support rotatably coupled to the bracket and disposed between the base and the ramp surface; and
    an adjusting mechanism configured to adjust an elevation angle of the ramp surface.

2. The orthopedic walking boot of claim 1, wherein the mechanically adjustable ramp insert comprises:
    a threaded shaft secured to the adjusting mechanism at a first end and configured to rotate with the adjusting mechanism;
    a first slider nut comprising internal threads and configured to move along the threaded shaft as the threaded shaft is rotated, wherein the first slider nut is rotatably coupled to the first support; and
    a stationary nut in physical contact with the threaded shaft and configured not to move along the threaded shaft as the threaded shaft is rotated, wherein the stationary nut is rotatably coupled to the second support.

3. The orthopedic walking boot of claim 2, wherein the first support is configured to move toward the second support as the threaded shaft is rotated, thereby causing mechanically adjustable ramp insert to elevate the ramp surface.

4. The orthopedic walking boot of claim 2, wherein the base comprises at least one guide within which an end of the first support is configured to travel as the ramp surface is elevated.

5. The orthopedic walking boot of claim 2, wherein the mechanically adjustable ramp insert further comprises a stopper in physical contact with a second end of the threaded shaft and configured to restrict movement of the threaded shaft in any direction normal to an axis of rotation of the threaded shaft.

6. The orthopedic walking boot of claim 1, wherein the elevation angle is continuously variable within a range of angles.

7. The orthopedic walking boot of claim 6, wherein the range of angles is between approximately 0 degrees to approximately 30 degrees.

8. The orthopedic walking boot of claim 1, further comprising a removably attached liner disposed on the ramp surface.

9. The orthopedic walking boot of claim 8, wherein the removably attached liner is constructed from a memory foam material.

10. The orthopedic walking boot of claim 1, wherein the bracket comprises at least one peg configured to slide within the at least one guide as the ramp surface is elevated.

11. The orthopedic walking boot of claim 1, wherein the at least one guide comprises a slot in the ramp surface.

12. The orthopedic walking boot of claim 1, wherein the mechanically adjustable ramp insert further comprises an anterior portion and a hinge that physically couples the anterior portion to the ramp surface.

13. The orthopedic walking boot of claim 1, wherein one or both of the first support and the second support comprises a multi-ply leaf spring configured to attenuate a portion of physical loads transmitted to the user's foot when the user is walking.

14. The orthopedic walking boot of claim 1, wherein the user's foot is in a state of plantarflexion when disposed on the ramp surface.

15. The orthopedic walking boot of claim 1, further comprising a mechanically adjustable lift configured to cause the mechanically adjustable ramp insert to descend within the housing as the ramp surface is elevated such that vertical displacement of the user's foot caused by elevation of the ramp surface is substantially attenuated.

16. The orthopedic walking boot of claim 1, wherein the adjusting mechanism comprises a dial.

17. A method for adjusting an orthopedic walking boot, comprising:
    adjusting an adjusting mechanism disposed on a housing of the orthopedic walking boot thereby achieving a desired elevation angle of a ramp surface of a mechanically adjustable ramp insert of the orthopedic walking boot; and
    inserting a user's foot into the housing and disposing the user's foot on the ramp surface such that the user's foot is supported in a position of plantarflexion determined at least in part by the desired elevation angle of the ramp surface,
    wherein, within the mechanically adjustable ramp insert, adjusting the adjusting mechanism causes a bracket, rotatably coupled to each of a first support and a second support disposed between the base and the ramp surface, to slide along at least one guide in the ramp surface as the ramp surface is elevated.

18. The method of claim 17, wherein, within the mechanically adjustable ramp insert, adjusting the adjusting mechanism further causes:
    a threaded shaft, secured to the adjusting mechanism at a first end, to rotate with the adjusting mechanism; and
    a first slider nut, rotatably coupled to the first support and comprising internal threads, to move along the threaded shaft as the threaded shaft is rotated,
    wherein a stationary nut, rotatably coupled to the second support and in physical contact with the threaded shaft, is configured not to move along the threaded shaft as the threaded shaft is rotated.

19. The method of claim 17, wherein, within the mechanically adjustable ramp insert, adjusting the adjusting mechanism further causes the first support to move toward the second support as the threaded shaft is rotated, thereby causing mechanically adjustable ramp insert to elevate the ramp surface.

\* \* \* \* \*